(12) United States Patent
Kiniwa et al.

(10) Patent No.: US 11,252,382 B1
(45) Date of Patent: *Feb. 15, 2022

(54) 3 MOS CAMERA

(71) Applicant: PANASONIC I-PRO SENSING SOLUTIONS CO., LTD., Fukuoka (JP)

(72) Inventors: Yuji Kiniwa, Fukuoka (JP); Yota Hashimoto, Fukuoka (JP); Yuuichi Takenaga, Fukuoka (JP)

(73) Assignee: PANASONIC I-PRO SENSING SOLUTIONS CO., LTD., Fukuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/132,554

(22) Filed: Dec. 23, 2020

(30) Foreign Application Priority Data

Jul. 31, 2020 (JP) .............................. JP2020-131042

(51) Int. Cl.
*H04N 9/097* (2006.01)
*H04N 5/225* (2006.01)
*H04N 5/232* (2006.01)
*H04N 5/265* (2006.01)
*H04N 9/04* (2006.01)
*G02B 5/26* (2006.01)
*G02B 5/20* (2006.01)
(Continued)

(52) U.S. Cl.
CPC ............ *H04N 9/097* (2013.01); *G02B 5/208* (2013.01); *G02B 5/26* (2013.01); *G02B 27/1013* (2013.01); *H04N 5/2258* (2013.01); *H04N 5/23235* (2013.01); *H04N 5/265* (2013.01); *H04N 5/33* (2013.01); *H04N 5/332* (2013.01); *H04N 5/335* (2013.01); *H04N 9/0451* (2018.08); *H04N 9/04553* (2018.08); *H04N 9/04557* (2018.08); *A61B 5/0071* (2013.01)

(58) Field of Classification Search
None
See application file for complete search history.

(56) References Cited

U.S. PATENT DOCUMENTS

| | | | |
|---|---|---|---|
| 11,089,271 B2* | 8/2021 | Kiniwa | H04N 5/332 |
| 2015/0085174 A1* | 3/2015 | Shabtay | H04N 5/332 |
| | | | 348/336 |

(Continued)

FOREIGN PATENT DOCUMENTS

JP 2016-075825 5/2016

*Primary Examiner* — David N Werner
(74) *Attorney, Agent, or Firm* — Greenblum & Bernstein, P.L.C.

(57) ABSTRACT

A 3 MOS camera includes a first prism that causes a first image sensor to receive IR light of light from an observation part, a second prism that causes a second image sensor to receive visible light of A % (A: a predetermined real number) of the light from the observation part, a third prism that causes a third image sensor to receive remaining visible light of (100–A) % of the light from the observation part, and a video signal processor that combines a color video signal based on imaging outputs of the second image sensor and the third image sensor and an IR video signal based on an imaging output of the first image sensor and outputs the combined signal to a monitor, the second image sensor and the third image sensor being respectively bonded to positions optically shifted by substantially one pixel.

5 Claims, 12 Drawing Sheets

(51) Int. Cl.
 *G02B 27/10* (2006.01)
 *H04N 5/33* (2006.01)
 *H04N 5/335* (2011.01)
 *A61B 5/00* (2006.01)

(56) References Cited

U.S. PATENT DOCUMENTS

2016/0292506 A1\* 10/2016 Rudmann ............ H04N 5/2226
2017/0219834 A1   8/2017 Horiguchi et al.
2017/0237887 A1\* 8/2017 Tanaka ................... G03B 15/05
                                                    348/164
2020/0120314 A1\* 4/2020 Yoshizaki ............ H04N 5/2354

\* cited by examiner

GREEN PIXEL OF ONE BAYER ARRAY IS DISPOSED ON
BLUE PIXEL/RED PIXEL OF THE OTHER BAYER ARRAY

… (1)

3 MOS CAMERA

BACKGROUND OF THE INVENTION

1. Field of the Invention

The present disclosure relates to a 3 MOS camera.

2. Background Art

In recent years, attention has been paid to a diagnosis method in which, at the time of surgery or examination, ICG (indocyanine green) is administered as a fluorescent reagent into a subject, and the ICG is excited by emission of excitation light or the like to capture and observe a near-infrared fluorescence image emitted by the ICG together with a subject image. For example, JP-A-2016-75825 discloses an imaging device having a blue separation prism that reflects a part of blue component light of incident light and near-infrared light in a specific wavelength region and transmits light other than the above light, a red separation prism that reflects a part of red component light of incident light and near-infrared light in a specific wavelength region and transmits light other than the above light, and a green separation prism into which the light transmitted through the red separation prism is incident.

In a configuration in JP-A-2016-75825, a partial light amount of the near-infrared light of light from a diseased part or the like is incident on each of the plurality of color separation prisms in a shared manner and imaged. For this reason, for example, there is a problem in that light specialized in the wavelength region of the near-infrared light cannot be received by a corresponding imaging element. Therefore, it is difficult to output a clearer fluorescence image of an observation part to which the fluorescent reagent is administered at the time of surgery or examination described above, and there is room for improvement in that a doctor or the like can more easily grasp the diseased part. Each of blue, red, and green lights is specially imaged. Therefore, there is room for improvement in enhancing resolution of a video by imaging visible light.

SUMMARY OF THE INVENTION

The present disclosure has been devised in view of the above-mentioned circumstances, and a purpose thereof is to provide a 3 MOS camera that achieves both generation of a clearer fluorescence video of an observation part to which a fluorescent reagent is administered and resolution enhancement of a color image of the observation part to assist a doctor or the like in easily grasping a diseased part.

The present disclosure provides a 3 MOS camera including a first prism that causes a first image sensor to receive IR light of light from an observation part, a second prism that causes a second image sensor to receive visible light of A % (A: a predetermined real number) of the light from the observation part, a third prism that causes a third image sensor to receive remaining visible light of (100−A) % of the light from the observation part, and a video signal processor that combines a color video signal based on imaging outputs of the second image sensor and the third image sensor and an IR video signal based on an imaging output of the first image sensor and outputs the combined signal to a monitor, the second image sensor and the third image sensor being respectively bonded to positions optically shifted by substantially one pixel.

According to the present disclosure, it is possible to achieve both the generation of the clearer fluorescence video of the observation part to which the fluorescent reagent is administered and the resolution enhancement of the color image of the observation part, and thus to assist the doctor or the like in easily grasping the diseased part.

DETAILED DESCRIPTION OF THE EXEMPLARY EMBODIMENT

Hereinafter, embodiments that specifically disclose a 3 MOS camera according to the present disclosure will be described in detail with reference to drawings as appropriate. However, more detailed description than necessary may be omitted. For example, detailed description of a well-known matter and redundant description of substantially the same configuration may be omitted. This is to prevent the following description from being unnecessarily redundant and to facilitate understanding by those skilled in the art. The accompanying drawings and the following description are provided for those skilled in the art to fully understand the present disclosure, and are not intended to limit subject matters described in claims thereby.

Figure 1A:
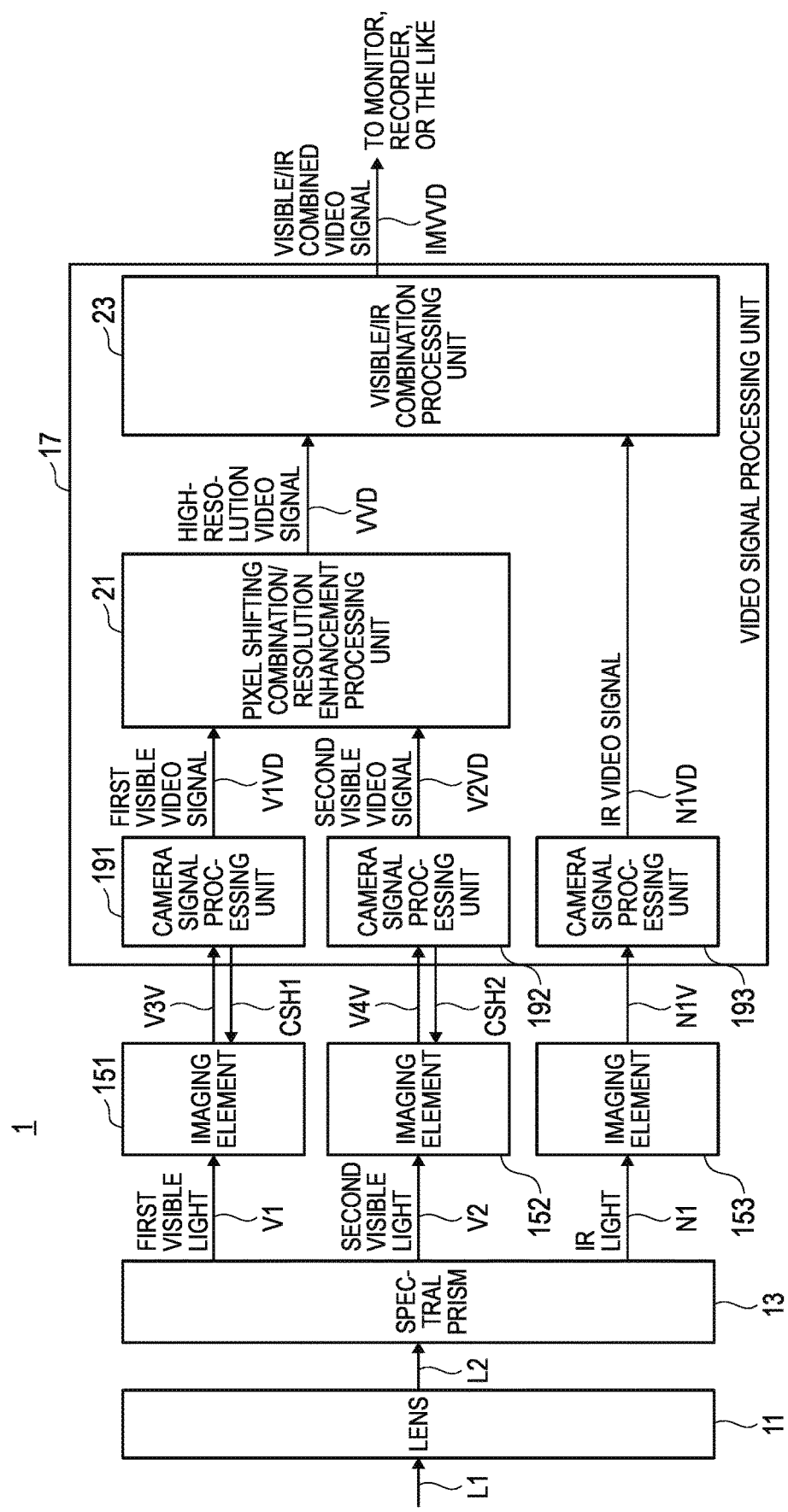
FIG. 1A is a block diagram showing an internal configuration example of a 3 MOS camera according to a first embodiment.

FIG. 1A is a block diagram showing an internal configuration example of a 3 MOS camera 1 according to a first embodiment.

Figure 1B:
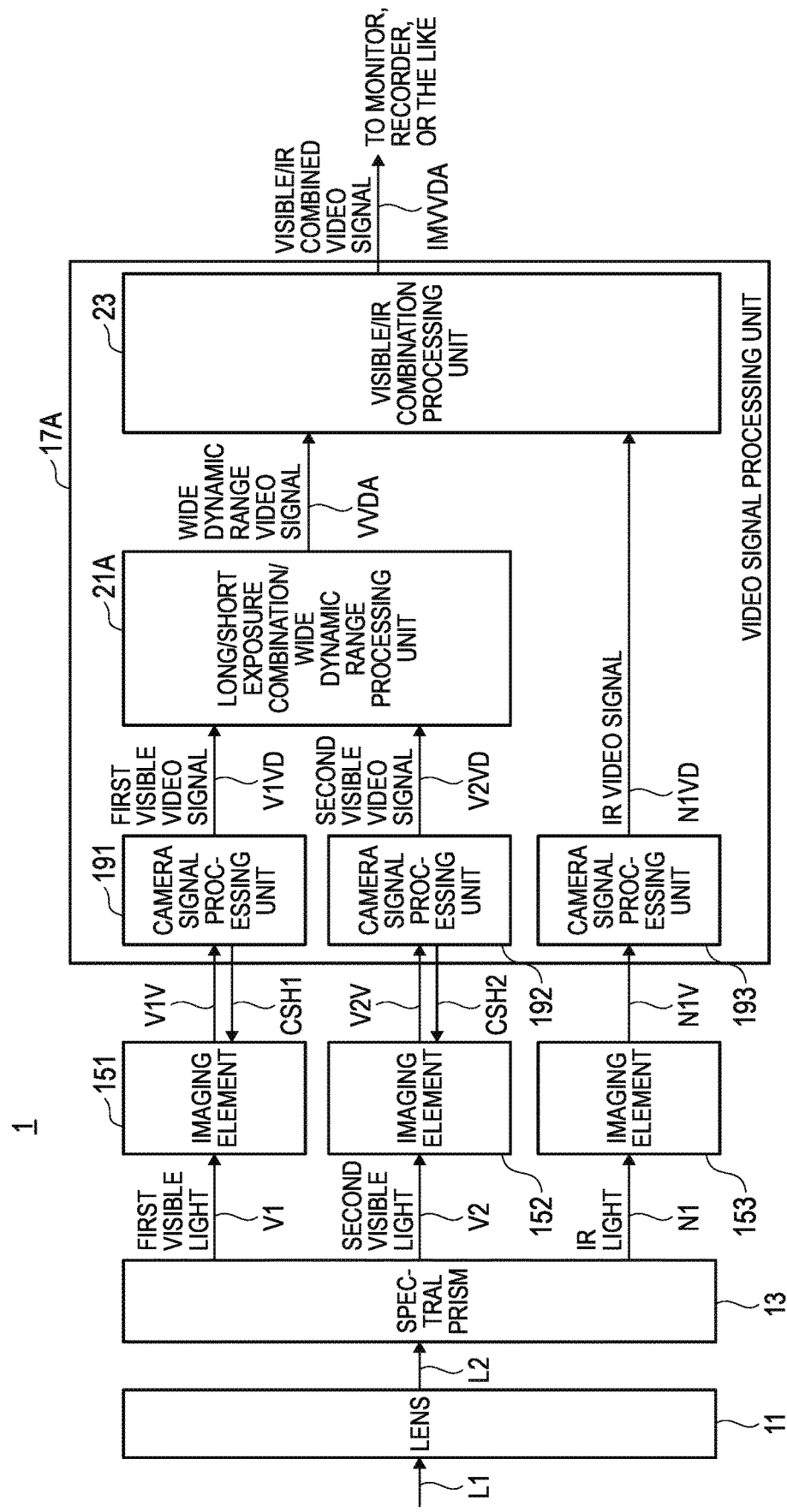
FIG. 1B is a block diagram showing another internal configuration example of the 3 MOS camera 1 according to the first embodiment.

FIG. 1B is a block diagram showing another internal configuration example of the 3 MOS camera 1 according to the first embodiment. The 3 MOS camera 1 includes a lens 11, a spectral prism 13, imaging elements 151, 152, and 153, and a video signal processing unit 17. The video signal processing unit 17 includes camera signal processing units 191, 192, and 193, a pixel shifting combination/resolution enhancement processing unit 21, and a visible/IR combination processing unit 23. As shown in FIG. 1B, the 3 MOS camera 1 may include a video signal processing unit 17A (refer to FIG. 1B) having a long/short exposure combination/wide dynamic range processing unit 21A, instead of the video signal processing unit 17 (refer to FIG. 1A). Although not shown, the 3 MOS camera 1 may include both the video signal processing unit 17 (refer to FIG. 1A) and the video signal processing unit 17A (refer to FIG. 1B). Each configuration will be described in detail.

The 3 MOS camera 1 is used for a medical observation system in which excitation light in a predetermined wavelength band (for example, 760 nm to 800 nm) is emitted to a fluorescent reagent (for example, indocyanine green; hereinafter referred to as "ICG") administered in advance to an observation part (for example, diseased part) in a subject such as a patient and the observation part that emits fluorescent light on a long wavelength side (for example, 820 to 860 nm) based on the excitation light is imaged, at the time of surgery or examination, for example. An image (for example, video of the observation part) captured by the 3 MOS camera 1 is displayed on a monitor MN1 (refer to FIG. 9) and assists a user such as a doctor in executing a medical procedure. The spectral prism 13 will be described as examples used in the medical observation system described above. However, the use thereof is not limited to medical usage and the prism may be used for industrial usage.

Although not shown in FIG. 1, a part of an objective side (in other words, tip side) of the 3 MOS camera 1 with respect to the lens 11 is configured by a scope that is inserted through the observation part (for example, diseased part; the same applies hereinafter). This scope is, for example, a main portion of a medical instrument such as a rigid endoscope inserted into the observation part and is a light guide member capable of guiding light L1 from the observation part to the lens 11.

The lens 11 is attached to the objective side (in other words, tip side) of the spectral prism 13 and collects the light L1 from the observation part (for example, reflected light at the observation part). Collected light L2 is incident on the spectral prism 13.

The spectral prism 13 receives the light L2 from the observation part and splits the light into first visible light V1, a second visible light V2, and IR light N1. The spectral prism 13 has a configuration having an IR prism 31, visible prisms 32 and 33 (refer to FIG. 2). The first visible light V1 is incident on the imaging element 151 disposed so as to face the visible prism 32. The second visible light V2 is incident on the imaging element 152 disposed so as to face the visible prism 33. The IR light N1 is incident on the imaging element 153 disposed so as to face the IR prism 31. A detailed structural example of the spectral prism 13 will be described below with reference to FIG. 2.

The imaging element 151 as an example of a second image sensor includes, for example, a charge coupled device (CCD) or a complementary metal oxide semiconductor (CMOS) in which a plurality of pixels suitable for imaging visible light are arranged, and an exposure control circuit (not shown) using an electronic shutter. In the CCD or CMOS constituting the imaging element 151, at least a microlens, a color filter, and a light receiving element are disposed, for example, corresponding to each pixel. The microlens collects incident light (visible light). The color filter transmits visible light of a specific color component (wavelength) transmitted through the microlens. The color filter of the imaging element 151 is disposed in a Bayer array (refer to FIG. 3A) such as red (R), green (G), green (G), and blue (B). The specific color component indicates, for example, red (R), green (G), and blue (B). The light receiving element receives light of the specific color component (wavelength) transmitted through the color filter. The imaging element 151 is disposed so as to face the visible prism 32 (refer to FIG. 2). The imaging element 151 captures an image based on the first visible light V1 that is incident for a first exposure time determined by the exposure control circuit based on an exposure control signal CSH1 from the camera signal processing unit 191. The imaging element 151 generates a video signal V1V of the observation part by imaging and outputs the signal to the video signal processing unit 17.

The imaging element 152 as an example of a third image sensor includes, for example, a CCD or a CMOS in which a plurality of pixels suitable for imaging visible light are arranged, and an exposure control circuit (not shown) using an electronic shutter. In the CCD or CMOS constituting the imaging element 152, at least a microlens, a color filter, and a light receiving element are arranged, for example, corresponding to each pixel. The microlens collects incident light (visible light). The color filter transmits visible light of a specific color component (wavelength) transmitted through the microlens. The color filter of the imaging element 152 is disposed in the Bayer array (refer to FIG. 3A) such as red (R), green (G), green (G), and blue (B). The specific color component indicates, for example, red (R), green (G), and blue (B). The light receiving element receives light of the specific color component (wavelength) transmitted through the color filter. The imaging element 152 is disposed so as to face the visible prism 33 (refer to FIG. 2). The imaging element 152 captures an image based on the second visible light V2 that is incident for a second exposure time determined by the exposure control circuit based on an exposure control signal CSH2 from the camera signal processing unit 192.

The imaging element 152 generates a video signal V2V of the observation part by imaging and outputs the signal to the video signal processing unit 17.

The imaging element 153 as an example of a first image sensor includes, for example, a CCD or a CMOS in which a plurality of pixels suitable for imaging IR light are arranged. The imaging element 153 is disposed so as to face the IR prism 31 (refer to FIG. 2). The imaging element 153 captures an image based on the incident IR light N1. The imaging element 153 generates a video signal N1V of the observation part by imaging and outputs the signal to the video signal processing unit 17.

The video signal processing unit 17 is configured of a processor such as a digital signal processor (DSP) or a field programmable gate array (FPGA). The camera signal processing units 191 to 193, the pixel shifting combination/resolution enhancement processing unit 21, and the visible/IR combination processing unit 23 are executed by the processor described above.

The camera signal processing unit 191 performs various types of camera signal processing using the video signal V1V from the imaging element 151 to generate a first visible video signal V1VD of the observation part, and outputs the signal to the pixel shifting combination/resolution enhancement processing unit 21 or the long/short exposure combination/wide dynamic range processing unit 21A. The camera signal processing unit 191 generates the exposure control signal CSH1 for determining the first exposure time of the imaging element 151 and outputs the signal to the imaging element 151. The imaging element 151 controls the exposure time of the first visible light V1 based on the exposure control signal CSH1.

The camera signal processing unit 192 performs various types of camera signal processing using the video signal V2V from the imaging element 152 to generate a second visible video signal V2VD of the observation part, and outputs the signal to the pixel shifting combination/resolution enhancement processing unit 21 or the long/short exposure combination/wide dynamic range processing unit 21A. Although the details will be described below, brightness (sensitivity) of the first visible video signal V1VD and brightness of the second visible video signal V2VD may be substantially the same (including the same) or may be different. In particular, the closer the brightness (sensitivity) of the first visible video signal V1VD and the brightness of the second visible video signal V2VD are to substantially the same (including the same), the higher an effect of resolution enhancement is. The camera signal processing unit 192 generates the exposure control signal CSH2 for determining the exposure time of the imaging element 152 and outputs the signal to the imaging element 152.

The imaging element 152 controls the second exposure time of the second visible light V2 based on the exposure control signal CSH2. Although the details will be described below, the first exposure time and the second exposure time may be the same (refer to FIG. 5) or may be different (refer to FIGS. 6 to 8), and the same applies hereinafter.

The camera signal processing unit 193 performs various types of camera signal processing using the video signal N1V from the imaging element 153 to generate an IR video signal N1VD of the observation part, and outputs the signal to the visible/IR combination processing unit 23.

The pixel shifting combination/resolution enhancement processing unit 21 receives two video signals (specifically, the first visible video signal V1VD from the camera signal processing unit 191 and the second visible video signal V2VD from the camera signal processing unit 192). The closer the brightness of the first visible video signal V1VD and the brightness of the second visible video signal V2VD are to the same, the higher the effect of resolution enhancement by the pixel shifting combination/resolution enhancement processing unit 21 is. Combination/pixel interpolation processing is performed in consideration of a spatial positional relationship between the first visible video signal V1VD and the second visible video signal V2VD, and thus it is possible to generate a high-resolution video signal VVD with high resolution.

The pixel shifting combination/resolution enhancement processing unit 21 performs combination processing on the received two input video signals (that is, combination of the first visible video signal V1VD generated by the camera signal processing unit 191 based on the imaging of the imaging element 151 bonded to the visible prism 32 and the second visible video signal V2VD generated by the camera signal processing unit 192 based on the imaging of the imaging element 152 bonded to the visible prism 33) to generate the high-resolution video signal VVD. With the combination processing (refer to above) on the received two input video signals, the pixel shifting combination/resolution enhancement processing unit 21 can generate the high-resolution video signal VVD having higher resolution than the first visible video signal V1VD or the second visible video signal V2VD. The pixel shifting combination/resolution enhancement processing unit 21 outputs the high-resolution video signal VVD to the visible/IR combination processing unit 23. The generation of the high-resolution video signal VVD by the pixel shifting combination/resolution enhancement processing unit 21 will be described below with reference to FIG. 3A.

In the 3 MOS camera 1, the video signal processing unit 17 generates the high-resolution video signal VVD by pixel shifting. Therefore, in the spectral prism 13 (refer to FIG. 2), when the imaging element 151 on which the first visible light V1 is incident and the imaging element 152 on which the second visible light V2 is incident are respectively bonded to the corresponding visible prisms 32 and 33, it is necessary to optically shift positions of the imaging element 151 and the imaging element 152 by substantially one pixel (for example, in the horizontal or vertical direction, or in both directions) to perform the bonding (refer to FIG. 3A). Accordingly, the pixel shifting combination/resolution enhancement processing unit 21 can generate the high-resolution video signal VVD by the pixel shifting based on the imaging of the imaging elements 151 and 152 which are disposed in an optically shifted manner by substantially one pixel (refer to above). The substantially one pixel includes one pixel, may not be exactly one pixel, and may include, for example, a distance deviation of one pixel plus or minus 0.25 pixels.

The closer an amount of pixel shifting is to one pixel, the higher the effect of resolution enhancement by the pixel shifting combination/resolution enhancement processing unit 21 is.

The long/short exposure combination/wide dynamic range processing unit 21A receives and superimposes the two video signals having different brightness (sensitivity) (specifically, the first visible video signal V1VD from the camera signal processing unit 191 and the second visible video signal V2VD from the camera signal processing unit 192) for combining the signals to generate a wide dynamic range video signal VVDA. The long/short exposure combination/wide dynamic range processing unit 21A superimposes and combines the two video signals having different brightness (sensitivity) and thus can generate the wide dynamic range video signal VVDA with an apparently wider dynamic range than the first visible video signal V1VD or the second visible video signal V2VD. The long/short exposure combination/wide dynamic range processing unit 21A outputs the wide dynamic range video signal VVDA to the visible/IR combination processing unit 23.

The visible/IR combination processing unit 23 receives and superimposes the high-resolution video signal VVD from the pixel shifting combination/resolution enhancement processing unit 21 and the IR video signal N1VD from the camera signal processing unit 193 for combining the signals to generated a visible/IR combined video signal IMVVD. With the visible/IR combined video signal IMVVD, the resolution is enhanced by the combination processing after the pixel shifting. Therefore, a state around the observation part (for example, surgical field) becomes visually clear and a state of the diseased part can be clarified in detail by the fluorescent light emission of the fluorescent reagent such as ICG (refer to FIG. 9). The visible/IR combination processing unit 23 may output the visible/IR combined video signal IMVVD to the monitor MN1 or send the signal to a recording device (not shown) for accumulation.

The monitor MN1 constitutes, for example, an image console (not shown) disposed in a surgery room at the time of surgery or examination, and displays the visible/IR combined video signal IMVVD of the observation part generated by the 3 MOS camera 1. Accordingly, the user such as doctor can visually recognize the visible/IR combined video signal IMVVD displayed on the monitor MN1 to grasp in detail the part that emits fluorescent light in the observation part. The recording device is a recorder capable of recording data of the visible/IR combined video signal IMVVD generated by the 3 MOS camera 1, for example.

Figure 2:
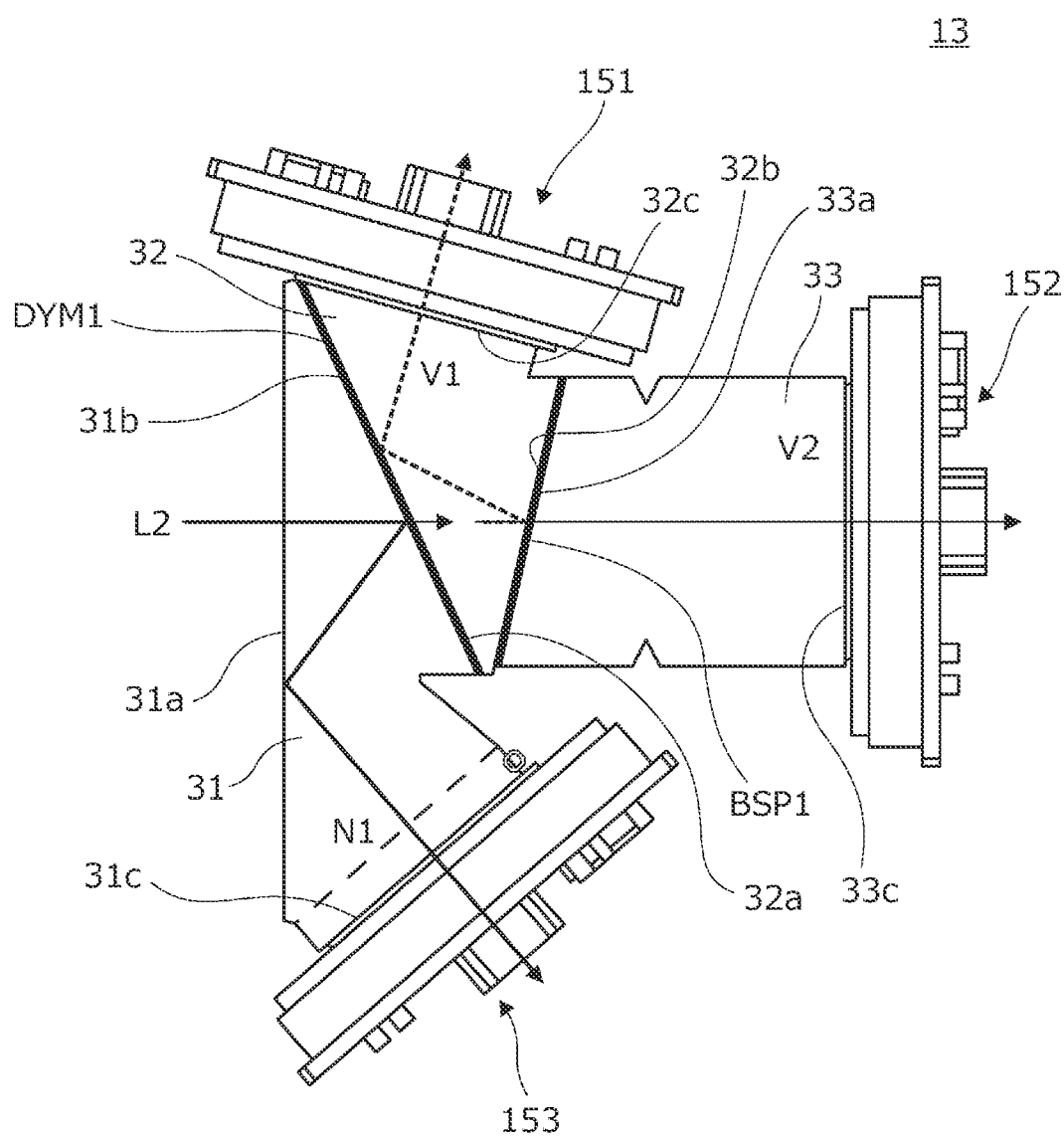
FIG. 2 is a diagram showing a structural example of a spectral prism shown in FIG. 1.

FIG. 2 is a diagram showing a structural example of the spectral prism 13 shown in FIG. 1. Hereinafter, the structural example of the spectral prism 13 shown in FIG. 1 will be mainly described with reference to FIG. 2. The spectral prism 13 includes the IR prism 31 (an example of a first prism), the visible prism 32 (an example of a second prism), and the visible prism 33 (an example of a third prism). The IR prism 31, the visible prism 32, and the visible prism 33 are sequentially assembled in an optical axis direction of the light L2 collected by the lens 11.

The IR prism 31 as an example of the first prism includes an incident surface 31a on which the light L2 is incident, a reflection surface 31b on which a dichroic mirror DYM1 that reflects the IR light of the light L2 is formed, and an emission surface 31c from which the IR light is emitted. The dichroic mirror DYM1 (an example of first reflection film) is formed on the reflection surface 31b by vapor deposition or the like, reflects the IR light (for example, IR light in the wavelength band of 800 nm or more) of the light L2, and transmits light (for example, light of about 400 nm to 800 nm) other than the IR light of the light L2 (refer to FIG. 4A). Specifically, the IR light (refer to above) of the light L2 incident on the incident surface 31a of the IR prism 31 is reflected by the reflection surface 31b. This IR light is reflected by the reflection surface 31b, is then totally reflected by the incident surface 31a of the IR prism 31, and is incident on the imaging element 153 through the emission surface 31c.

Figure 4A:
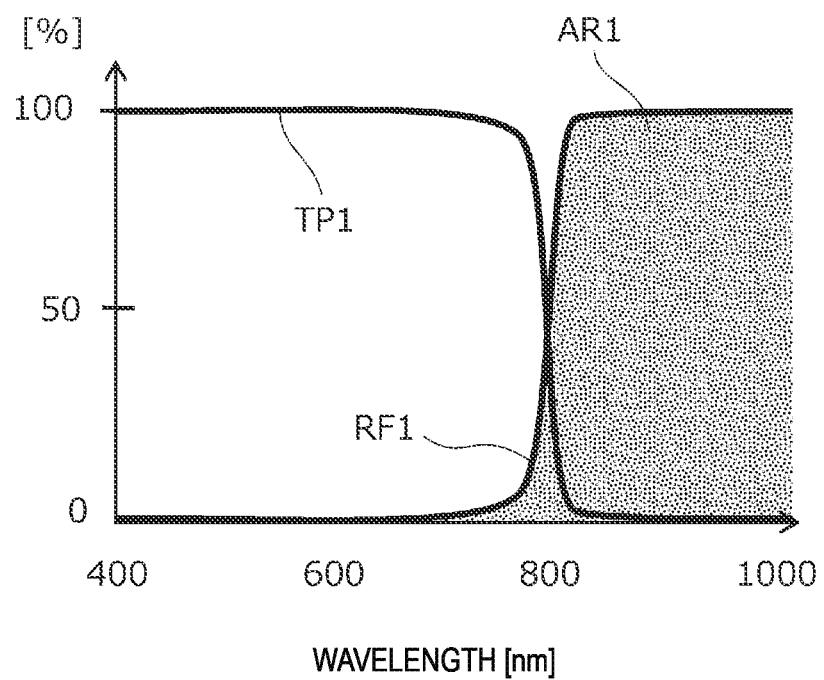
FIG. 4A is a graph showing an example of spectral characteristics of a dichroic mirror.

FIG. 4A is a graph showing an example of spectral characteristics of the dichroic mirror DYM1. The horizontal axis of FIG. 4A indicates wavelength [nm: nanometer (the same applies hereinafter)], and the vertical axis indicates reflectance or transmittance. A characteristic TP1 indicates the transmittance of the dichroic mirror DYM1. According to the characteristic TP1, the dichroic mirror DYM1 can transmit the light of about 400 nm to 800 nm. A characteristic RF1 indicates the reflectance of the dichroic mirror DYM1. According to the characteristic RF1, the dichroic mirror DYM1 can reflect the IR light of 800 nm or more. Therefore, all the IR light having a light amount indicated by an area AR1 (in other words, the IR light of the light L2) can be incident on the imaging element 153.

The visible prism 32 as an example of the second prism includes an incident surface 32a on which the light (an example of first transmitted light) transmitted through the dichroic mirror DYM1 is incident, a reflection surface 32b on which a beam splitter BSP1 for reflecting a partial light amount of the transmitted light (specifically, visible light) is formed, and an emission surface 32c from which reflected visible light of the partial light amount is emitted. The beam splitter BSP1 (an example of second reflection film) is formed on the reflection surface 32b by vapor deposition or the like, reflects visible light having a partial (for example, around A % of the light incident on the incident surface 32a; A is a predetermined real number, for example, 50) light amount of the visible light incident on the incident surface 32a, and transmits visible light having a remaining (100-A) % (for example, around 50% of the light incident on the incident surface 32a) light amount thereof (refer to FIG. 4B). Specifically, the visible light having the partial (for example, 50%) light amount of the visible light incident on the incident surface 32a of the visible prism 32 is reflected by the reflection surface 32b. This part of the visible light is reflected by the reflection surface 32b, is then totally reflected by the incident surface 32a of the visible prism 32, and is incident on the imaging element 151 through the emission surface 32c. In the spectral prism 13 shown in FIG. 1, a ratio of visible light reflected by the beam splitter BSP1 is not limited to 50% and may be in a range of 30% to 50%, for example.

The visible prism 33 as an example of the third prism has an incident surface 33a on which the visible light having the remaining light amount transmitted through the beam splitter BSP1 is incident and an emission surface 33c from which the visible light having the remaining light amount is emitted. Specifically, the visible light having the remaining light amount transmitted through the beam splitter BSP1 is incident on the visible prism 33, is emitted as it is, and is incident on the imaging element 152 (refer to FIG. 4B).

Figure 4B:
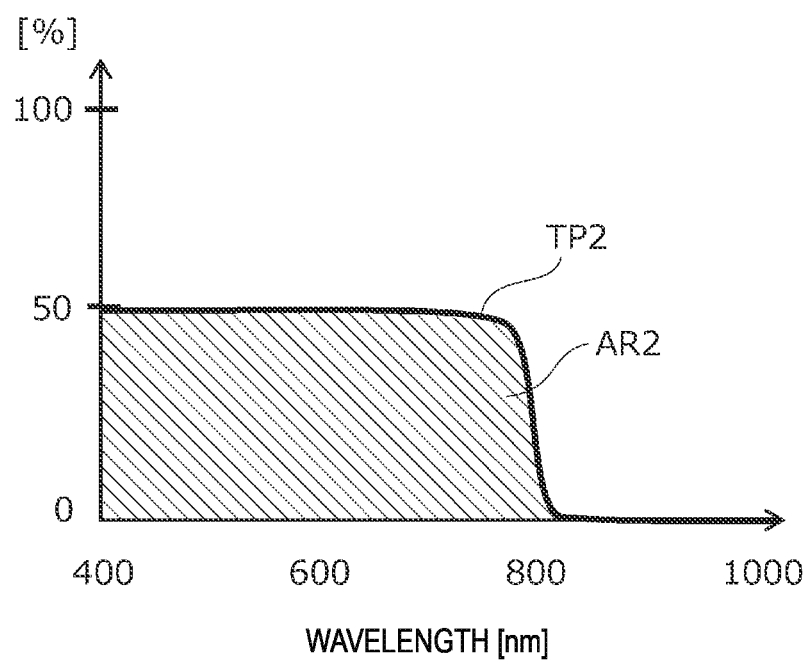
FIG. 4B is a graph showing an example of spectral characteristics of a beam splitter.

FIG. 4B is a graph showing an example of spectral characteristics of the beam splitter BSP1. The horizontal axis of FIG. 4B indicates wavelength [nm], and the vertical axis indicates reflectance or transmittance. A characteristic TP2 indicates transmittance and reflectance (about 50% at 400 nm to 800 nm) of the beam splitter BSP1 in the spectral prism 13 shown in FIG. 2. With the characteristic TP2, the beam splitter BSP1 as an example of the second reflection film can reflect light having a light amount of about 50% (mainly visible light) of the light of about 400 nm to 800 nm and can transmit light having a remaining light amount of about 50% (mainly visible light) thereof. Therefore, visible light having a light amount indicated by an area AR2 (for example, visible light having light amount of about 50%) can be incident on the imaging element 151. The visible light having the light amount indicated by the area AR2 (for example, visible light having light amount of about 50%) can be incident on the imaging element 152.

Figure 3A:
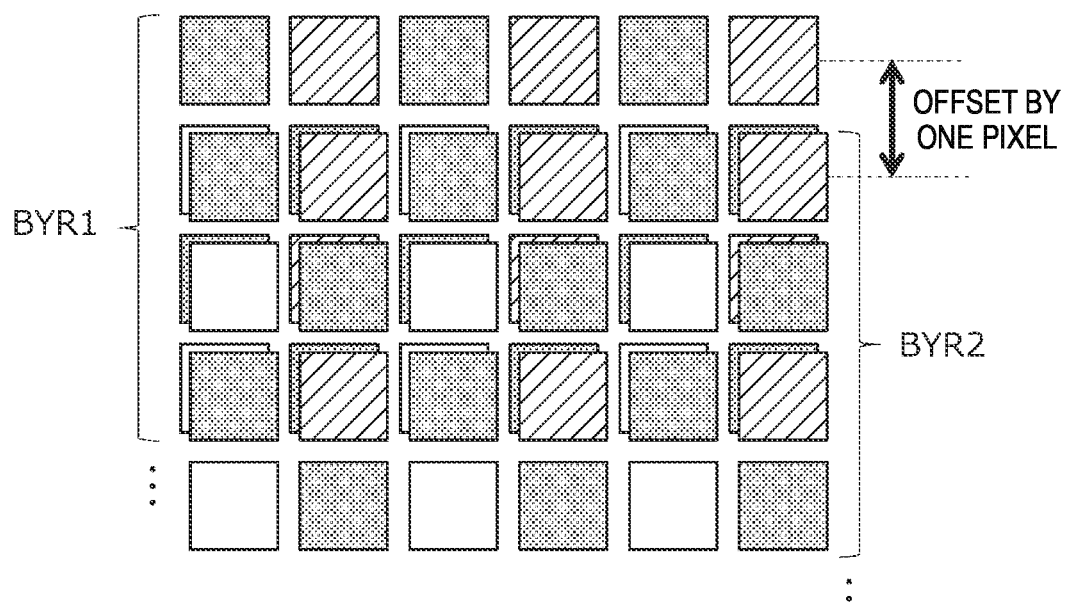
FIG. 3A is a diagram showing an arrangement example of color filters of imaging elements 151 and 152.

Next, the arrangement of color filters BYR1 and BYR2 of the imaging elements 151 and 152 will be described with reference to FIG. 3A. FIG. 3A is a diagram showing an arrangement example of the color filters BYR1 and BYR2 of the imaging elements 151 and 152. The color filter BYR1 is a color filter constituting the imaging element 151 and is disposed in the Bayer array consisting of the color filters of red (R), green (G), green (G), and blue (B) in any four adjacent pixels in the horizontal and vertical directions, for example. In the Bayer array, more green (G) is disposed than red (R) and blue (B) in any four pixels. This is because human vision is known to react most sensitively to green (G). Similarly, the color filter BYR2 is a color filter constituting the imaging element 152 and is disposed in the Bayer array consisting of the color filters of red (R), green (G), green (G), and blue (B) in any four adjacent pixels in the horizontal and vertical directions, for example.

As shown in FIG. 3A, the imaging elements 151 and 152 are disposed with an offset of one pixel, and thus the color filters BYR1 and BYR2 are disposed so as to be offset by one pixel. Although FIG. 3A shows an example in which the offset of one pixel is added, the color filters BYR1 and BYR2 may be disposed with an offset of substantially one pixel (refer to above). Therefore, with the pixel shifting of the offset of substantially one pixel (refer to above), the green (G) pixel of one Bayer array (for example, the color filter BYR1) is disposed on the blue (B) pixel or the red (R) pixel of the other Bayer array (for example, the color filter BYR2). In other words, the green (G) color filter is disposed for all pixels. Accordingly, the pixel shifting combination/resolution enhancement processing unit 21 that receives the first visible video signal V1VD and the second visible video signal V2VD can generate the high-resolution video signal VVD having high resolution as compared with a video signal in a case where the pixel shifting by substantially one pixel is not performed, by selectively using light transmitted through the green (G) color filter, which has the highest ratio of contributing to resolution of a luminance signal in each pixel, of the color filters BYR1 and BYR2 of the Bayer array stacked in two layers (refer to FIG. 3A).

Figure 3B:
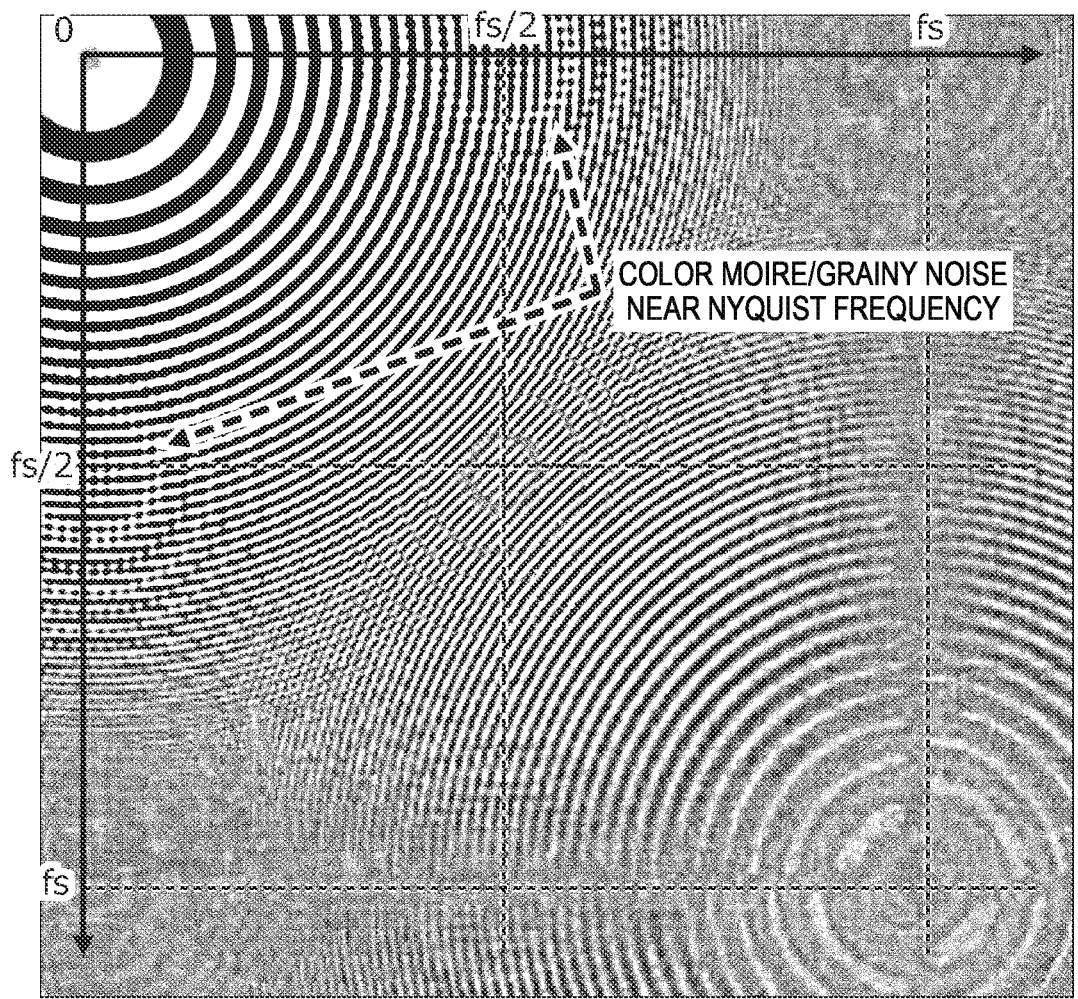
FIG. 3B is an explanatory diagram of a problem in a case where the color filters of the imaging elements 151 and 152 are configured in a Bayer array and are disposed with half pixel shifting.

A problem in a case where the color filters of the imaging elements 151 and 152 are disposed with a pixel shifting offset by a half pixel will be described with reference to FIG. 3B. FIG. 3B is an explanatory diagram of a problem in a case where the color filters BYR1 and BYR2 of the imaging elements 151 and 152 are configured in the Bayer array and disposed with the half pixel shifting. The horizontal axis and the vertical axis of FIG. 3B are both frequencies, where fs indicates sampling frequency and fs/2 indicates Nyquist frequency.

In a case where the color filters of the imaging elements 151 and 152 are stacked and disposed with the pixel shifting offset by the half pixel, it is found that false color or moire, which is not present in the subject, is detected near the Nyquist frequency (fs/2) as shown in FIG. 3B. When such false color or moire is detected, the image quality of the color video signal deteriorates. On the other hand, in order to solve such a problem, in the first embodiment, the color filters BYR1 and BYR2 are disposed with the optical offset of one pixel as shown in FIG. 3A. Accordingly, in the high-resolution video signal VVD generated by the pixel shifting combination/resolution enhancement processing unit 21, there is no detection of the false color or moire as shown in FIG. 3B near the Nyquist frequency (fs/2) and the image quality is accurately enhanced.

Figure 5:
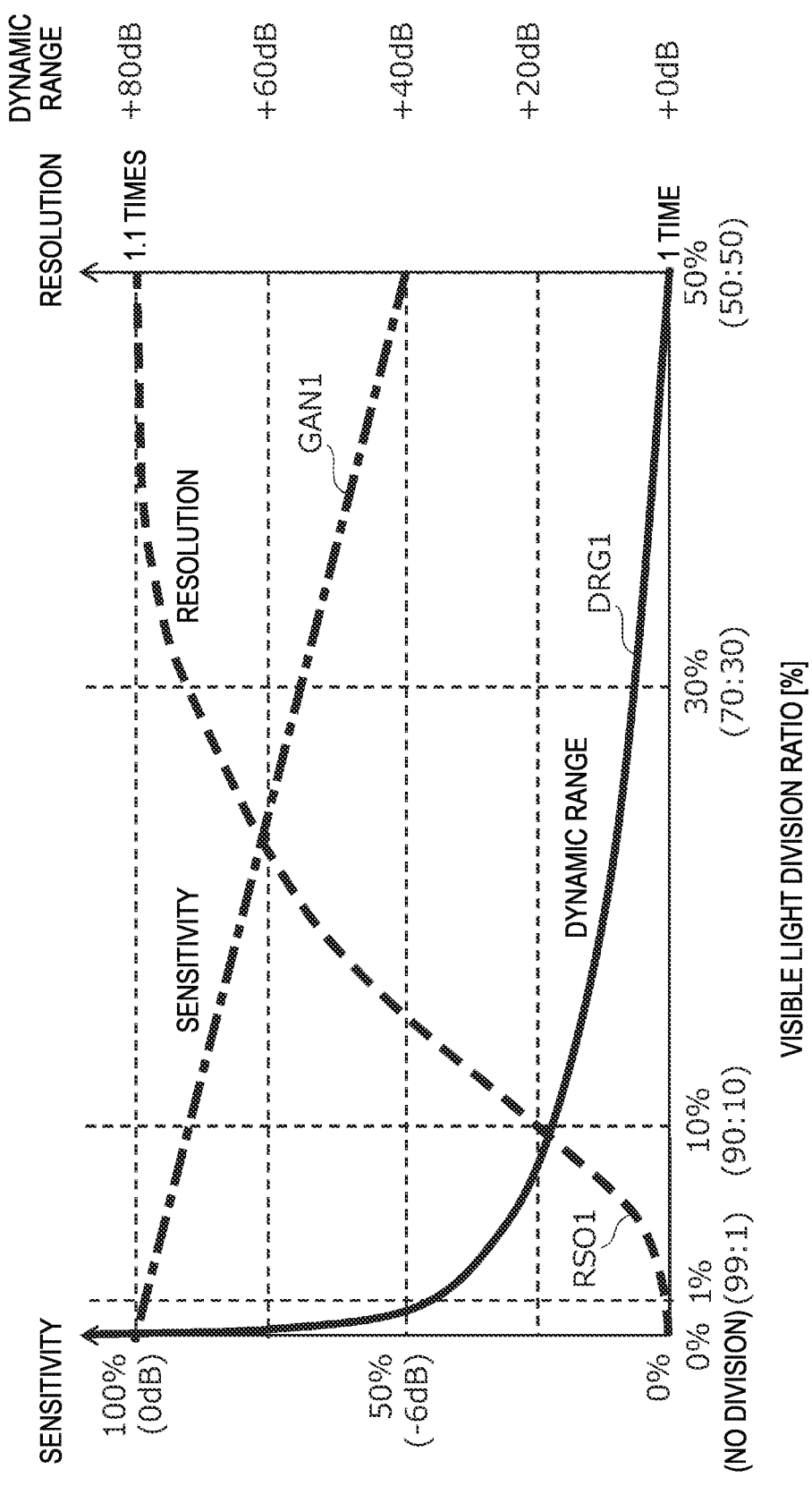
FIG. 5 is a graph showing an example of a relationship between visible light division ratio and sensitivity, dynamic range, and resolution in a case where exposure times of second visible light and first visible light are the same.

FIG. 5 is a graph showing an example of a relationship between visible light division ratio and sensitivity GAN1, dynamic range DRG1, and resolution RSO1 in a case where exposure times of the second visible light V2 and the first visible light V1 are the same. The horizontal axis of FIG. 5 is the visible light division ratio. In other words, the visible light division ratio is a ratio at which the beam splitter BSP1 reflects the visible light transmitted through the dichroic mirror DYM1. For example, in a case where the visible light division ratio is 10% (that is, 90:10), the beam splitter BSP1 reflects the visible light of 10% of the visible light transmitted through the dichroic mirror DYM1 and transmits the visible light of 90% thereof. That is, the ratio light amount of the second visible light V2:light amount of the first visible light V1 is 90:10. Another visible light division ratio can be considered in the same manner as the specific example described above. The vertical axis of FIG. 5 shows the sensitivity GAN1, the dynamic range DRG1, and the resolution RSO1 of the high-resolution video signal VVD generated by the video signal processing unit 17.

FIG. 5 shows an example in which the exposure times for the imaging elements 152 and 151 by the electronic shutter are controlled to be the same. Therefore, it is considered that the sensitivity GAN1 transitions according to a characteristic (for example, a linear function) that the sensitivity is the maximum as the visible light division ratio is smaller (for example, the maximum (100%) and the brightest when the ratio is 0%) and the sensitivity is the minimum (for example, the darkest at 50%) when the ratio is 50%. This is because the sensitivity is determined by the brightness of the brighter second visible light V2 of the brightness of the first visible video signal V1VD based on the first visible light V1 and the brightness of the second visible video signal V2VD based on the second visible light V2.

It is considered that the dynamic range DRG1 transitions according to a characteristic that the dynamic range increases similarly as the visible light division ratio is smaller in a range larger than zero (for example, about +80 dB when the ratio is 0.01%) and the dynamic range is the minimum (for example, 0 dB) when the ratio is 50%. This is because a difference between a dark portion and a bright portion tends to widen as the visible light division ratio is smaller in the high-resolution video signal VVD.

It is considered that the resolution RSO1 transitions according to a characteristic that the resolution is the minimum contrarily as the visible light division ratio is smaller (for example, the maximum of 1 time when the ratio is 0%) and the resolution is the maximum (for example, 1.1 times) when the ratio is 50%. This is because a difference in pixel value between adjacent pixels is small as the visible light division ratio is larger and thus it is easy to realize high resolution by pixel shifting.

Figure 6:
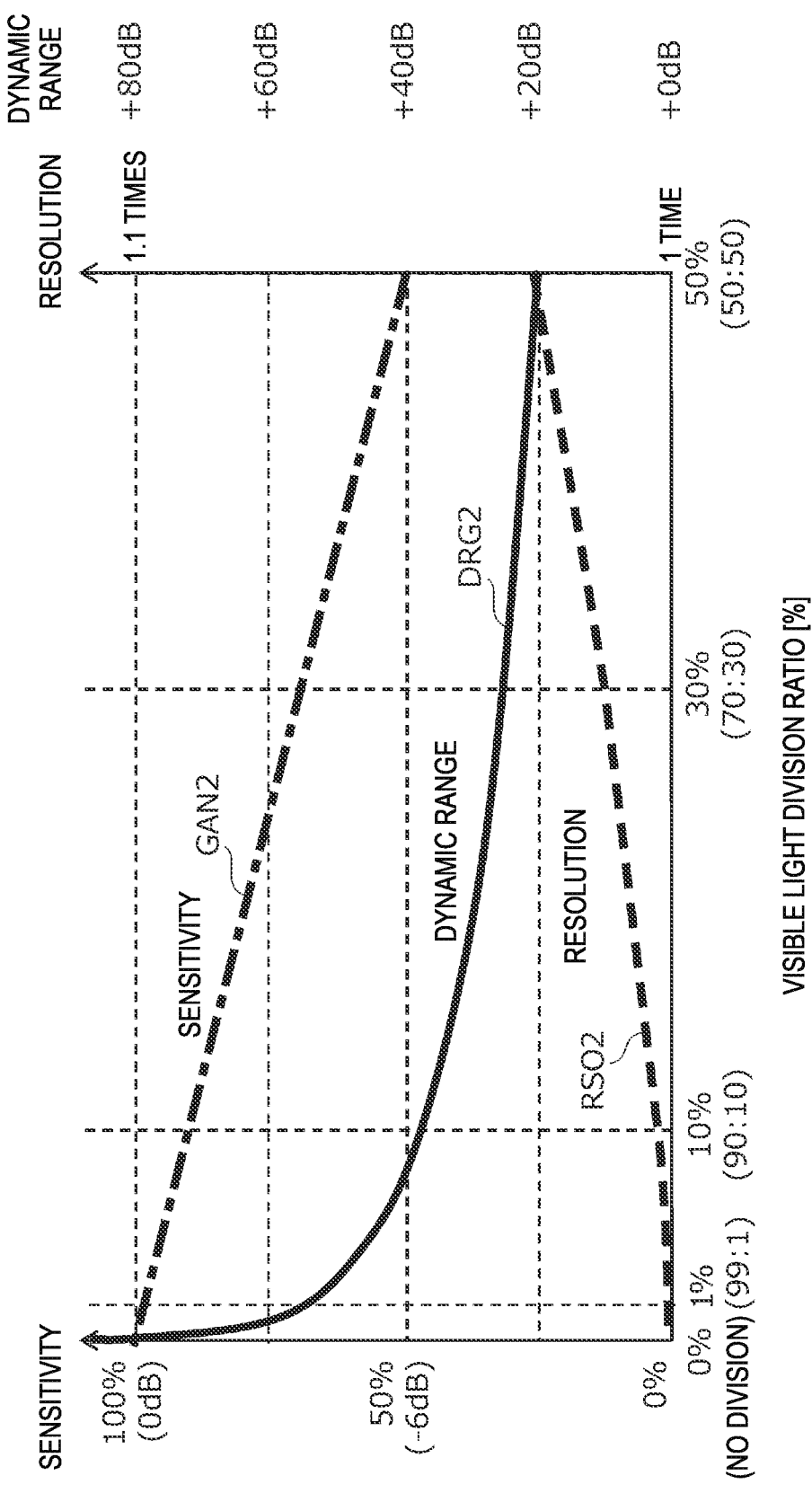
FIG. 6 is a graph showing an example of the relationship between visible light division ratio and sensitivity, dynamic range, and resolution in a case where a ratio of the exposure times of the second visible light and the first visible light is 10:1.

FIG. 6 is a graph showing an example of a relationship between visible light division ratio and sensitivity GAN2, dynamic range DRG2, and resolution RSO2 in a case where a ratio of the exposure times of the second visible light V2 and the first visible light V1 is 10:1. The horizontal axis of FIG. 6 is the visible light division ratio, and description thereof will be omitted since the description is the same as that in FIG. 5. The vertical axis of FIG. 6 shows the sensitivity GAN2, the dynamic range DRG2, and the resolution RSO2 of the high-resolution video signal VVD generated by the video signal processing unit 17.

FIG. 6 shows an example in which a difference is provided such that a ratio of the exposure times for the imaging elements 152 and 151 by the electronic shutter is 10:1. It is considered, as in the case of the sensitivity GAN1 shown in FIG. 5, that the sensitivity GAN2 transitions according to a characteristic (for example, a linear function) that the sensitivity is the maximum as the visible light division ratio is smaller (for example, the maximum (100%) and the brightest when the ratio is 0%) and the sensitivity is the minimum (for example, the darkest at 50%) when the ratio is 50%. This is because a brightness ratio of the second visible video signal V2VD and the first visible video signal V1VD is obtained by multiplying the ratio of the exposure times for the imaging elements 152 and 151 of 10:1 by a light amount ratio of the second visible light V2 and the first visible light V1, and the sensitivity is determined by the brightness of the brighter second visible video signal V2VD of the second visible video signal V2VD and the first visible video signal V1VD.

When a difference is provided such that the ratio of the exposure times for the imaging elements 152 and 151 is, for example, 10:1 as compared with when the exposure time thereof is the same, it is considered that the difference between the bright portion and the dark portion is likely to appear further clearly and thus it is possible to gain more dynamic range, in the high-resolution video signal VVD. Therefore, it is considered that the dynamic range DRG2 transitions according to a characteristic that the dynamic range increases similarly as the visible light division ratio is smaller in a range larger than zero (for example, about +80 dB when the ratio is 0.1%) and the dynamic range is the minimum (for example, +20 dB) when the ratio is 50%. That is, it is possible to gain +20 dB even with a minimum value in the example of FIG. 6.

When the difference is provided such that the ratio of the exposure times for the imaging elements 152 and 151 by the electronic shutter is 10:1, it is considered that the ratio light amount of light incident on the imaging element 152:light amount of light incident on the imaging element 151=100:1 in a case where the visible light division ratio is 10% (the ratio second visible light V2:first visible light V1=90:10). That is, the dark portion is hardly projected by the first visible light V1 and the bright portion is hardly projected by the second visible light V2, and thus it can be considered that it is almost difficult to gain a resolution when two video signals are superimposed. Therefore, it is considered that the resolution RSO2 transitions over small values (for example, the minimum of 1 time at 0% and about 1.02 times at 50%) regardless of the visible light division ratio.

Figure 7:
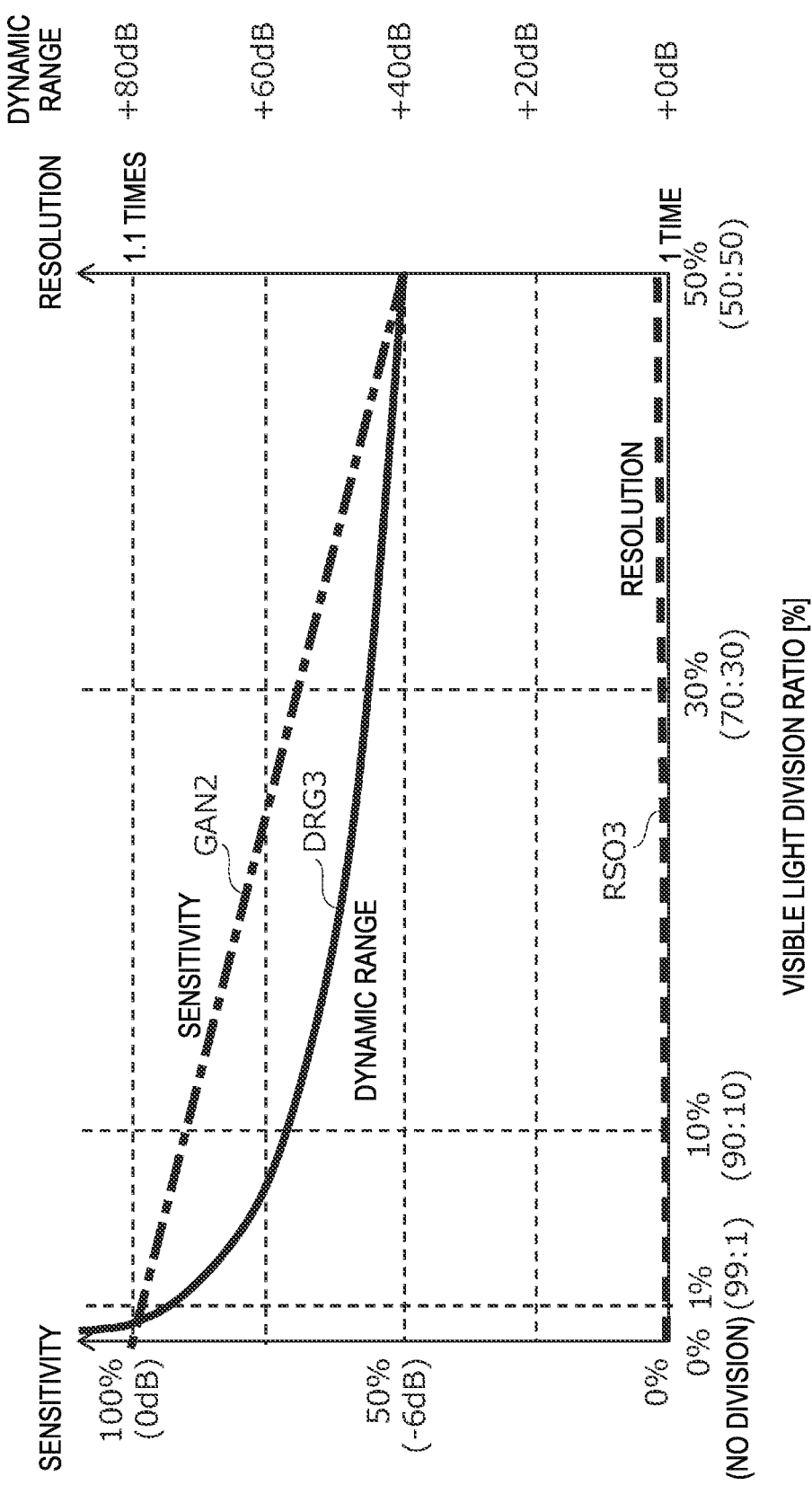
FIG. 7 is a graph showing an example of the relationship between visible light division ratio and sensitivity, dynamic range, and resolution in a case where the ratio of the exposure times of the second visible light and the first visible light is 100:1.

FIG. 7 is a graph showing an example of a relationship between visible light division ratio and sensitivity GAN2, dynamic range DRG3, and resolution RSO3 in a case where the ratio of the exposure times of the second visible light V2 and the first visible light V1 is 100:1. The horizontal axis of FIG. 7 is the visible light division ratio, and description thereof will be omitted since the description is the same as that in FIG. 5. The vertical axis of FIG. 7 shows the sensitivity GAN2, the dynamic range DRG3, and the resolution RSO3 of the high-resolution video signal VVD generated by the video signal processing unit 17.

FIG. 7 shows an example in which a considerable difference is provided such that the ratio of the exposure times for the imaging elements 152 and 151 by the electronic shutter is 100:1. It is considered, as in the case of the sensitivity GAN2 shown in FIG. 6, that the sensitivity GAN2 transitions according to a characteristic (for example, a linear function) that the sensitivity is the maximum as the visible light division ratio is smaller (for example, the maximum (100%) and the brightest when the ratio is 0%) and the sensitivity is the minimum (for example, the darkest at 50%) when the ratio is 50%.

This is because a brightness ratio of the second visible video signal V2VD and the first visible video signal V1VD is obtained by multiplying the ratio of the exposure times for the imaging elements 152 and 151 of 100:1 by a light amount ratio of the second visible light V2 and the first visible light V1, and the sensitivity is determined by the brightness of the brighter second visible video signal V2VD of the second visible video signal V2VD and the first visible video signal V1VD.

When a considerable difference is provided such that the ratio of the exposure times for the imaging elements 152 and 151 is, for example, 100:1 as compared with when the exposure time thereof is the same, it is considered that the difference between the bright portion and the dark portion is likely to appear furthermore clearly and thus it is possible to gain more dynamic range, in the high-resolution video signal VVD. Therefore, it is considered that the dynamic range DRG3 transitions according to a characteristic that the dynamic range increases similarly as the visible light division ratio is smaller in a range larger than zero (for example, about +80 dB when the ratio is 1%) and the dynamic range is the minimum (for example, +40 dB) when the ratio is 50%. That is, it is possible to gain +40 dB even with a minimum value in the example of FIG. 7.

When the difference is provided such that the ratio of the exposure times for the imaging elements 152 and 151 by the electronic shutter is 100:1, it is considered that the ratio light amount of light incident on the imaging element 152:light amount of light incident on the imaging element 151=1000:1 in the case where the visible light division ratio is 10% (the ratio second visible light V2:first visible light V1=90:10). That is, the dark portion is hardly projected since the second visible light V2 is too bright and the bright portion is hardly projected since the first visible light V1 is too dark, and thus it can be considered that it is almost difficult to gain a resolution when two video signals are superimposed as compared with the example of FIG. 6. Therefore, it is considered that the resolution RSO3 transitions over small values (for example, the minimum of 1 time at 0% and about 1.001 times at 50%) regardless of the visible light division ratio.

Figure 8:
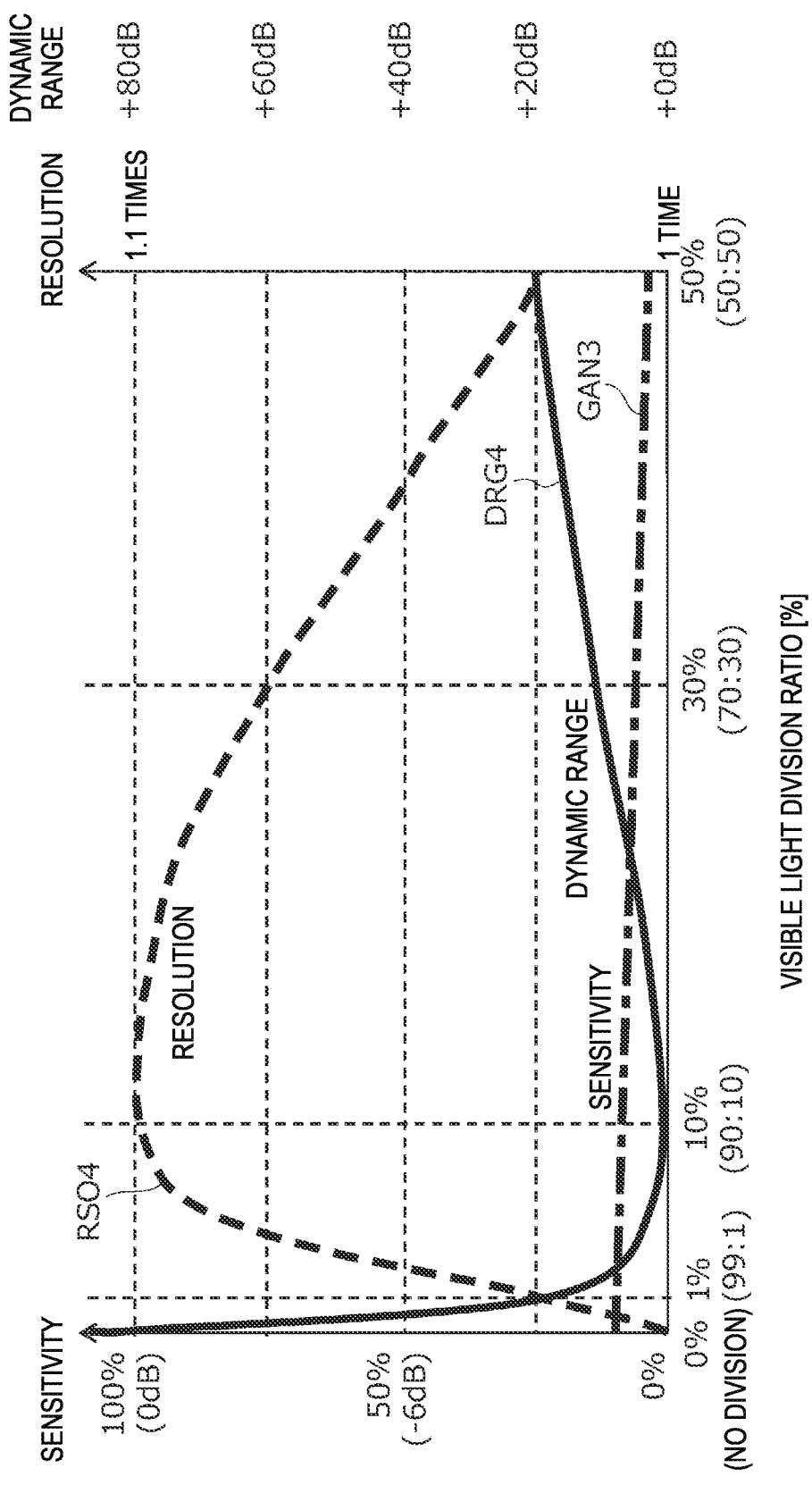
FIG. 8 is a graph showing an example of the relationship between visible light division ratio and sensitivity, dynamic range, and resolution in a case where the ratio of the exposure times of the second visible light and the first visible light is 1:10.

FIG. 8 is a graph showing an example of a relationship between visible light division ratio and sensitivity GAN3, dynamic range DRG4, and resolution RSO4 in a case where the ratio of the exposure times of the second visible light V2 and the first visible light V1 is 1:10. The horizontal axis of FIG. 8 is the visible light division ratio, and description thereof will be omitted since the description is the same as that in FIG. 5. The vertical axis of FIG. 8 shows the sensitivity GAN3, the dynamic range DRG4, and the resolution RSO4 of the high-resolution video signal VVD generated by the video signal processing unit 17.

FIG. 8 shows an example in which a difference is provided such that the ratio of the exposure times for the imaging elements 152 and 151 by the electronic shutter is 1:10. Contrary to the example of FIG. 6, when the difference is provided such that the ratio of the exposure times for the imaging elements 152 and 151 is, for example, 1:10, it is considered that the light amount of light incident on the imaging element 152 and the light amount of light incident on the imaging element 151 are substantially equal due to cancellation of the visible light division ratio and the exposure time ratio in the case where the visible light division ratio is 10% (second visible light V2:first visible light V1=90:10), for example. Therefore, it is considered that the sensitivity GAN3 transitions according to a characteristic that the sensitivity transitions substantially constant so as to be the minimum when the visible light division ratio is from 0% to 10% (in other words, in a case where light amounts incident on the imaging elements 152 and 151 do not change much) and the sensitivity increases monotonically in a linear function until the visible light division ratio is larger than 10% and reaches 50%. For example, the brightness is the maximum (50%, that is, −6 dB) when the visible light division ratio is 50%. This is because a brightness ratio of the second visible video signal V2VD and the first visible video signal V1VD is obtained by multiplying the ratio of the exposure times for the imaging elements 152 and 151 of 1:10 by a light amount ratio of the second visible light V2 and the first visible light V1, and the sensitivity is determined by the brightness of a brighter video signal of the second visible video signal V2VD and the first visible video signal V1VD.

When a difference is provided such that the ratio of the exposure times for the imaging elements 152 and 151 is, for example, 1:10 as compared with when the exposure time thereof is the same, it is considered that the difference in brightness is easier to obtain as the visible light division ratio is smaller in a range larger than 0%, but the difference between the bright portion and the dark portion is less likely to appear as the visible light division ratio is higher and thus it is difficult to gain more dynamic range, in the high-resolution video signal VVD. Therefore, the dynamic range DRG4 increases as the visible light division ratio is smaller in a range larger than 0% (for example, about +80 dB at 0.001%). However, when the visible light division ratio is 10%, the brightness of the second visible video signal V2VD and the brightness of the first visible video signal V1VD are substantially equal due to the cancellation of the visible light division ratio and the ratio of the exposure times for the imaging elements 152 and 151 of 1:10 and the dynamic range DRG4 is the minimum. When the visible light division ratio exceeds 10%, the brightness of the second visible video signal V2VD is different again from the brightness of the first visible video signal V1VD and the dynamic range DRG4 is large. When the visible light division ratio is 50%, the ratio of the brightness of the second visible video signal V2VD and the brightness of the first visible video signal V1VD is 1:10 by the multiplication of the ratio of the exposure times for the imaging elements 152 and 151 of 1:10 and the dynamic range is +20 dB.

When the difference is provided such that the ratio of the exposure times for the imaging elements 152 and 151 by the electronic shutter is 1:10, it is considered that the light amount of light incident on the imaging element 152 and the light amount of light incident on the imaging element 151 are substantially equal in the case where the visible light division ratio is 10% (the ratio second visible light V2:first visible light V1=90:10), for example (refer to above). That is, when the cancellation of the visible light division ratio and the exposure time ratio (1:10) occurs (for example, when the visible light division ratio is 10%), the first visible video signal V1VD based on the first visible light V1 and the second visible video signal V2VD based on the second visible light V2 have the same brightness. Therefore, it is considered that the resolution RSO4 transitions according to a characteristic that the resolution is the maximum and the resolution decreases from the maximum value at a visible light division ratio at which the cancellation is less likely to occur.

Figure 9:
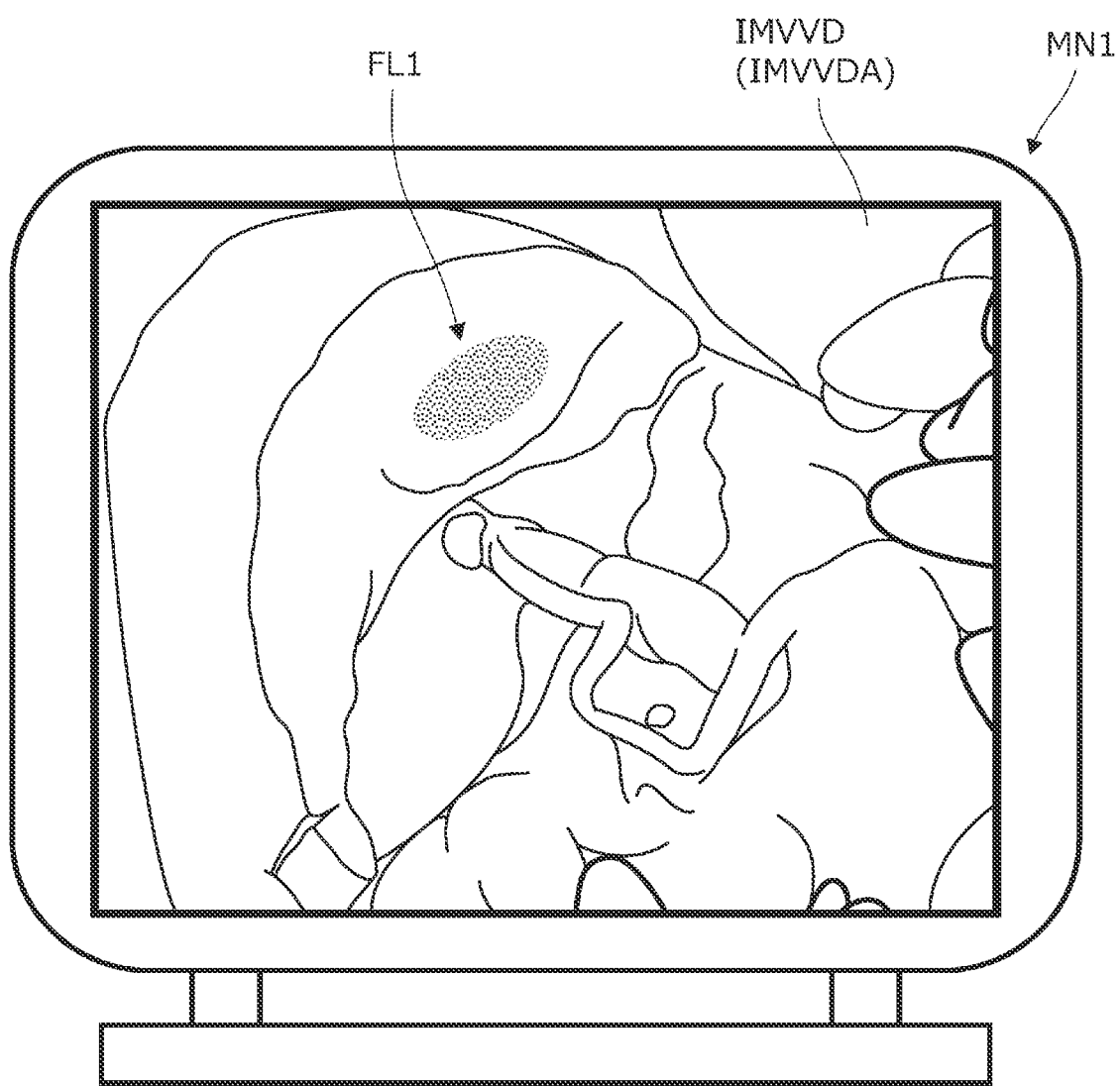
FIG. 9 is a diagram showing a display example of a visible/IR combined video signal generated by the 3 MOS camera according to the first embodiment on a monitor.

FIG. 9 is a diagram showing a display example of the visible/IR combined video signal IMVVD generated by the 3 MOS camera 1 according to the first embodiment on the monitor MN1. The visible/IR combined video signal IMVVD shown in FIG. 9 is generated based on imaging at the observation part (for example, around liver and pancreas) of the patient who is the subject and is displayed on the monitor MN1. In FIG. 9, the fluorescent reagent of ICG, which is administered in advance to the diseased part in a body of the patient before surgery or examination, emits light, and a place that emits the light (for example, diseased part FL1) is shown so as to be known in the visible/IR combined video signal IMVVD. The high-resolution video signal VVD having the high resolution is generated by the pixel shifting combination/resolution enhancement processing unit 21. Therefore, a clear video of the surgical field such as an observation target can be obtained with the visible/IR combined video signal IMVVD. In this manner, the 3 MOS camera 1 can generate the visible/IR combined video signal IMVVD, which allows the user such as doctor to grasp the details of the observation part with high image quality and to easily specify a position of the diseased part, and display the signal on the monitor MN1, at the time of surgery or examination, for example.

As described above, the 3 MOS camera 1 according to the first embodiment is provided with the first prism (for example, IR prism 31) that causes the imaging element 153 to receive the IR light of the light L2 from the observation part (for example, diseased part in the subject), the second prism (for example, visible prism 32) that reflects the visible light of A % of the light L2 from the observation part (for example, diseased part in the subject) and causes the imaging element 151 to receive the remaining (100−A) % thereof, and the third prism (for example, visible prism 33) that causes the imaging element 152 to receive the remaining visible light of (100−A) % thereof. The 3 MOS camera 1 is provided with the video signal processing unit 17 that combines the color video signal based on the imaging outputs of the imaging element 151 and the imaging element 152, which are respectively bonded to the positions optically shifted by substantially one pixel, and the IR video signal based on the imaging output of the imaging element 153, and outputs the combined signal to the monitor MN1.

Accordingly, the 3 MOS camera 1 can separate (split), by the spectral prism 13, the IR light specialized in a fluorescent region of the fluorescent reagent of the light from the observation part (for example, diseased part) to which the fluorescent reagent (for example, ICG) is administered in advance in the subject such as patient at the time of surgery or examination, for example.

The 3 MOS camera 1 can generate an RGB color video signal having high resolution based on the imaging outputs of the imaging elements 151 and 152, which are optically shifted by substantially one pixel, obtained by reflecting the part of the visible light of the light from the observation part and transmitting the remaining visible light thereof on the beam splitter BSP1. The 3 MOS camera 1 can generate an RGB color video signal with an expanded dynamic range by combining the imaging outputs of the imaging elements 151 and 152. The 3 MOS camera 1 can generate and output clearer fluorescence images in both the IR light and the visible light and thus achieve both the generation of a clearer fluorescence video of the observation part to which the fluorescent reagent is administered and the resolution enhancement of the color image of the observation part to assist the doctor or the like in easily grasping the diseased part.

The first reflection film (for example, dichroic mirror DYM1) that reflects the IR light is formed on the first prism. The second reflection film (for example, beam splitter BSP1) that reflects the visible light of A % of the visible light transmitted through the first reflection film and transmits the visible light of (100−A) % thereof is formed on the second prism. The visible light of (100−A) % that transmits through the second reflection film is incident on the third prism. The dichroic mirror DYM1 first splits the IR light of the light from the observation part (for example, diseased part), and the visible light transmitted through the dichroic mirror DYM1 is split by the beam splitter BSP1. Therefore, it is possible to improve the efficiency of the splitting in the dichroic mirror DYM1 and the beam splitter BSP1.

A value of A % and a value of the remaining (100−A) % are substantially equal. The A value becomes substantially 50, and light having equal brightness is incident on each of the color filters BYR1 and BYR2, which are optically shifted by substantially one pixel. Therefore, the 3 MOS camera 1 can effectively generate the highest resolution RGB color video signal.

The color filter BYR1 having red (R), green (G), and blue (B) of the imaging element 151 and the color filter BYR2 having red (R), green (G), and blue (B) of the imaging element 152 are disposed such that the green (G) color filter is located in each pixel. The video signal processing unit 17 selects a pixel value based on the green (G) color filter disposed so as to be located in each pixel and mainly uses the selected pixel value to generate the luminance signal among the color video signals. Accordingly, the video signal processing unit 17 can generate the high-resolution video signal VVD having high resolution as compared with the video signal in a case where the pixel shifting by substantially one pixel is not performed, by selectively using light transmitted through the green (G) color filter, which has the highest ratio of contributing to resolution of a luminance signal in each pixel, of the color filters BYR1 and BYR2 of the Bayer array stacked in two layers (refer to FIG. 3A). This is based on the fact that the green (G) color filter is known to have the highest proportion of contributing to the resolution of the luminance signal since human vision is most sensitive to green (G).

The imaging element 152 is disposed so as to be optically shifted by one pixel in at least one of the horizontal direction or the vertical direction with respect to the imaging element 151. Accordingly, the video signal processing unit can generate the high-resolution video signal VVD by the pixel shifting based on the imaging of the imaging elements 151 and 152 which are disposed in an optically shifted manner by substantially one pixel (refer to above).

The 3 MOS camera 1 controls the ratio of the exposure times of the imaging elements 151 and 152 to be the same or different. Accordingly, the 3 MOS camera 1 can generate high-quality video signals that adaptively realize sensitivity, dynamic range, and resolution fitted to the preference of the user according to the ratio of the exposure times of the imaging elements 151 and 152 and the reflectance of the visible light by the beam splitter BSP1 (refer to FIGS. 5 to 8).

Although various embodiments are described with reference to the drawings, it goes without saying that the present disclosure is not limited to such examples. It is obvious to those skilled in the art that various modification examples, change examples, substitution examples, addition examples, deletion examples, and equivalent examples can be conceived within the scope of the claims. Of course, it is understood that the various examples belong to the technical scope of the present disclosure. Further, the respective constituent elements in the various embodiments described above may be randomly combined in the scope of not departing from the spirit of the invention.

For example, the IR prism 31 is illustrated as an example of the first prism in the first embodiment described above, but the first prism may not be limited to the IR prism 31. For example, in a case where the first prism is not a visible prism that reflects the visible light, the first prism may be a prism that reflects the IR light and light in another wavelength band (for example, wavelength band of ultraviolet ray) other than the visible light of the light L2. Accordingly, instead of the IR video signal, a video obtained by combining, for example, a video signal based on imaging of the ultraviolet ray and an RGB color video signal with enhanced resolution and expanded dynamic range can be output to the monitor MN1 or the like.

In the spectral prism 13 shown in FIG. 2, an example in which the IR prism 31 is disposed most on the objective side has been described, but the IR prism 31 may not be disposed on the most objective side. For example, the IR prism 31 may be disposed at any of the positions of the visible prisms 32 and 33. With the bonding of the imaging elements 151 and 152 to the visible prisms 32 and 33 with the optical shift of substantially one pixel (refer to above), it is possible to obtain the same effect as that of the 3 MOS camera 1 according to the first embodiment described above regardless of the position of the IR prism 31 on the spectral prism 13.

The present disclosure is useful as the 3 MOS camera that achieves both the generation of the clearer fluorescence video of the observation part to which the fluorescent reagent is administered and the resolution enhancement of the color image of the observation part to assist the doctor or the like in easily grasping the diseased part.

The present application is based upon Japanese Patent Application (Patent Application No. 2020-131042 filed on Jul. 31, 2020), the content of which is incorporated herein by reference.

What is claimed is:
1. A 3 MOS camera comprising:
    a first prism that causes a first image sensor to receive IR light of light from an observation part;
    a second prism that causes a second image sensor to receive A % of the visible light of the light from the observation part, wherein A is a predetermined real number, and wherein the visible light from the observation part not received by the second image sensor is denoted as remaining visible light comprising (100−A) % of the visible light of the light from the observation part;
    a third prism that causes a third image sensor to receive the remaining visible light comprising (100−A) % of the visible light of the light from the observation part; and
    a video signal processor that
        combines a color video signal based on imaging outputs of the second image sensor and the third image sensor and an IR video signal based on an imaging output of the first image sensor to produce a combined signal, and
        outputs the combined signal to a monitor, wherein the second image sensor and the third image sensor are respectively bonded to positions optically shifted by substantially one pixel.

2. The 3 MOS camera according to claim 1, further comprising:
    a first reflection film formed on the first prism that
        reflects the IR light of the light from the observation part, and
        transmits the visible light of the light from the observation part therethrough;
    a second reflection film formed on the second prism that
        reflects the A % of the visible light of the light from the observation part transmitted through the first reflection film, and
        transmits the remaining visible light comprising (100−A) % of the visible light of the light from the observation part transmitted through the first reflection film; and
    wherein the remaining visible light comprising (100−A) % of the visible light of the light from the observation part transmitted through the second reflection film is incident on the third prism.

3. The 3 MOS camera according to claim 1, wherein a value of A % and a value of (100−A) % are substantially equal.

4. The 3 MOS camera according to claim 1, wherein
    the second image sensor comprises a color filter comprising red, green, and blue filters,
    the third image sensor comprises a color filter comprising red, green, and blue filters, of the third image sensor,
    the green color filter of the color filter of the second image sensor is located in each pixel of the second image sensor, the green color filter of the color filter of the third image sensor is located in each pixel of the third image sensor, and the video signal processor selects a pixel value based on the green color filters in each pixel to generate the color video signal.

5. The 3 MOS camera according to claim 4, wherein the third image sensor is disposed so as to be optically shifted by one pixel in at least one of a horizontal direction and a vertical direction with respect to the second image sensor.

* * * * *